(12) United States Patent
Thornton

(10) Patent No.: US 6,516,805 B1
(45) Date of Patent: Feb. 11, 2003

(54) APPARATUS FOR PREVENTION OF SNORING AND IMPROVED BREATHING DURING SLEEP

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 1058 days.

(21) Appl. No.: 08/828,523

(22) Filed: Mar. 31, 1997

Related U.S. Application Data

(63) Continuation of application No. 08/363,639, filed on Dec. 22, 1994, now abandoned, which is a continuation of application No. 08/129,598, filed on Sep. 29, 1993, now Pat. No. 5,427,117.

(51) Int. Cl.[7] ................................................. A61F 5/56

(52) U.S. Cl. .................. 128/848; 128/859; 128/861; 602/902

(58) Field of Search ............................ 128/846, 848, 128/859–862; 2/2; 602/902

(56) References Cited

U.S. PATENT DOCUMENTS

| 746,869 A | 8/1903 | Moulton |
| 774,446 A | 11/1904 | Moulton |
| 885,196 A | 4/1908 | Steil |
| 893,213 A | 7/1908 | Whiteway |
| 1,076,534 A | 10/1913 | Wallen |
| 1,146,264 A * | 7/1915 | Kelly ........................ 128/861 |
| 1,483,694 A | 2/1924 | Stukey |
| 1,649,664 A | 11/1927 | Carter |
| 1,674,336 A | 6/1928 | King |
| 2,171,695 A | 9/1939 | Harper |
| 2,178,128 A | 10/1939 | Waite ........................ 128/136 |
| 2,383,649 A | 8/1945 | Heidbrink ................... 128/142 |
| 2,424,533 A | 7/1947 | Faires ........................ 128/136 |
| 2,521,039 A | 9/1950 | Carpenter ................... 128/136 |
| 2,521,084 A | 9/1950 | Oberto ....................... 128/141 |
| 2,531,222 A | 11/1950 | Kesling ....................... 32/14 |
| 2,574,623 A | 11/1951 | Clyde ......................... 128/136 |
| 2,590,118 A | 3/1952 | Oddo, Jr. ..................... 128/136 |
| 2,627,268 A | 2/1953 | Leppich ....................... 128/136 |
| 2,833,278 A | 5/1958 | Ross .......................... 128/862 |

(List continued on next page.)

FOREIGN PATENT DOCUMENTS

| DE | 156627 | 12/1904 |
| DE | 2320501 | 11/1974 |
| DE | 3707952 | 9/1988 |
| EP | 0312368 | 4/1989 |
| EP | 0359135 | 3/1990 |
| GB | 1569129 | 6/1980 |

OTHER PUBLICATIONS

"Snoring," 13 Mayo Clinic Health Letter 7, Jul. 1995.
2–piece dental device manufacturing by Currie–Gibson Dental Laboratory, Inc. prior to Apr. 13, 1993.
Farrar & McCarty, A Clinical Outline of Temporomandibular Joint Diagnosis and Treatment, Normandie Study Group for TMJ Dysfunction, 1993.
Professional Positioners Brochure (date unknown).
Great Lakes Orthodontics, Ltd. Brochure, Nocturnal Airway Patency Appliance™ (NAPA), undated, 2 pages.
George, "Treatment of Snoring and Obstructive Sleep Apnea with a Dental Device," *General Denistry*, Jul.–Aug. 1993, 5 pages.
Schmidt–Nowara, et al., "Oral Appliances for the Treatment of Snoring and Obstructive Sleep Apnea: A Review," *Sleep*, vol. 18, No. 6, 1995, 10 pages.

*Primary Examiner*—Michael A. Brown
(74) *Attorney, Agent, or Firm*—Baker Botts L.L.P.

(57) ABSTRACT

A dental device is provided in which an upper arch (12) and a lower arch (14) are inserted in a user's mouth. A deformable material (20) is included with upper arch (12) and lower arch (14) so as to allow a user to form his or her own teeth molding. A post (16) extends from the upper arch (12) and contacts the lower arch (14) so as to extend the user's lower jaw forward, thereby reducing snoring.

20 Claims, 3 Drawing Sheets

U.S. PATENT DOCUMENTS

| | | | |
|---|---|---|---|
| 2,867,212 A | 1/1959 | Nunn, Jr. | 128/136 |
| 2,882,893 A | 4/1959 | Godfroy | 128/136 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallsheim | 128/136 |
| 3,277,892 A | 10/1966 | Tepper | 128/172.1 |
| 3,312,216 A | 4/1967 | Wallsheim | 128/136 |
| 3,321,832 A | 5/1967 | Weisberg | 32/32 |
| 3,434,470 A | 3/1969 | Strickland | 138/136 |
| 3,457,916 A | 7/1969 | Wolicki | 128/136 |
| 3,513,838 A | 5/1970 | Foderick | 128/861 |
| 3,522,805 A | 8/1970 | Wallshein | 128/136 |
| 3,854,208 A | 12/1974 | Arant | 32/19 |
| 3,864,832 A | 2/1975 | Carlson | 128/862 |
| 3,871,370 A | 3/1975 | McDonald | 128/136 |
| 3,884,226 A | 5/1975 | Tepper | 128/136 |
| 4,016,650 A | 4/1977 | Leusner et al. | |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,289,127 A | 9/1981 | Nelson | 128/207.14 |
| 4,304,227 A | 12/1981 | Samelson | 128/136 |
| 4,376,628 A | 3/1983 | Aardse | 128/861 |
| 4,382,783 A | 5/1983 | Rosenberg | 433/19 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,470,413 A | 9/1984 | Warncke | 128/201.18 |
| 4,495,945 A | 1/1985 | Liegner | 128/200.26 |
| 4,505,672 A * | 3/1985 | Kurz | 433/6 |
| 4,553,549 A | 11/1985 | Pope et al. | 128/421 |
| 4,568,280 A | 2/1986 | Ahlin | 433/6 |
| 4,569,342 A | 2/1986 | Von Nostitz | 128/862 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,669,459 A | 6/1987 | Spiewak et al. | 128/136 |
| 4,676,240 A | 6/1987 | Gardy | 128/207.14 |
| 4,715,368 A * | 12/1987 | George | 128/859 |
| 4,773,853 A | 9/1988 | Kussick | 433/6 |
| 4,799,500 A | 1/1989 | Newbury | 128/859 |
| 4,862,903 A | 9/1989 | Campbell | 128/861 |
| 4,901,737 A * | 2/1990 | Toone | 128/848 |
| 4,919,128 A | 4/1990 | Kopala et al. | 128/207.18 |
| 4,932,867 A | 6/1990 | Ueno | 433/69 |
| 4,955,393 A * | 9/1990 | Adell | 128/861 |
| RE33,442 E * | 11/1990 | George | 128/860 |
| 5,003,994 A | 4/1991 | Cook | 128/848 |
| 5,018,533 A | 5/1991 | Hawkins | 128/848 |
| 5,028,232 A | 7/1991 | Snow | 433/24 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,056,534 A | 10/1991 | Wright | 128/848 |
| 5,078,600 A | 1/1992 | Austin | 433/73 |
| 5,092,346 A * | 3/1992 | Hays | 128/861 |
| 5,103,838 A | 4/1992 | Yousif | 128/859 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Luth | 433/68 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A * | 5/1994 | Tomasi | 128/848 |
| 5,316,020 A | 5/1994 | Truffer | 128/848 |
| 5,365,945 A * | 11/1994 | Halstrom | 128/848 |
| 5,373,859 A | 12/1994 | Forney | 128/846 |
| 5,409,017 A | 4/1995 | Lowe | 128/848 |
| 5,427,117 A | 6/1995 | Thornton | 128/848 |
| 5,537,994 A | 7/1996 | Thornton | 128/204.18 |
| 5,566,683 A | 10/1996 | Thornton | 128/848 |

* cited by examiner

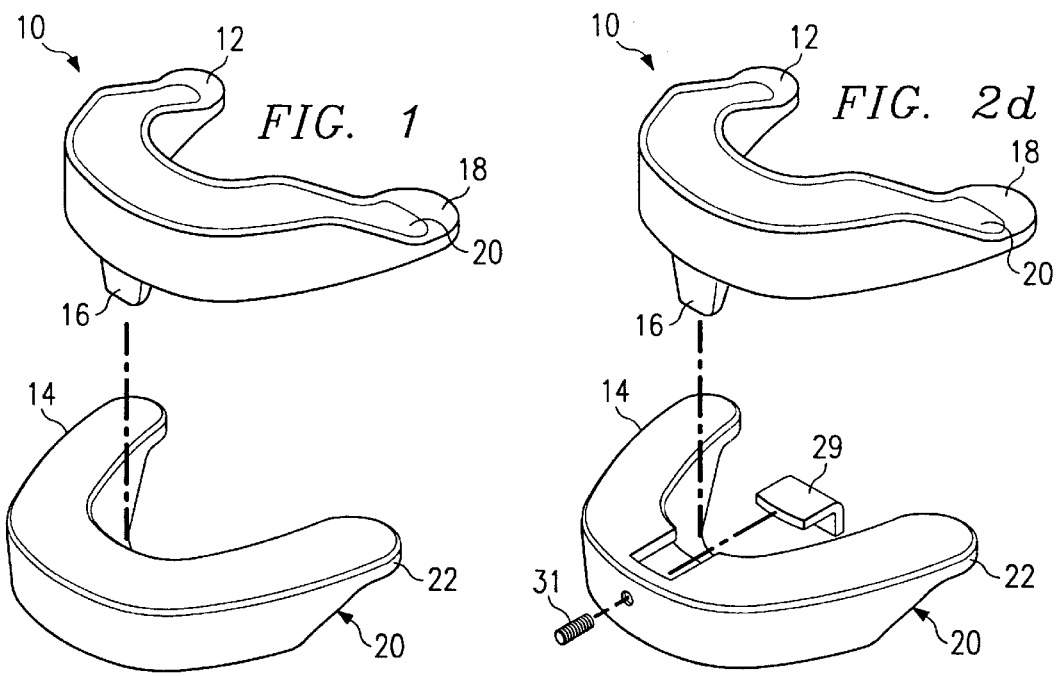
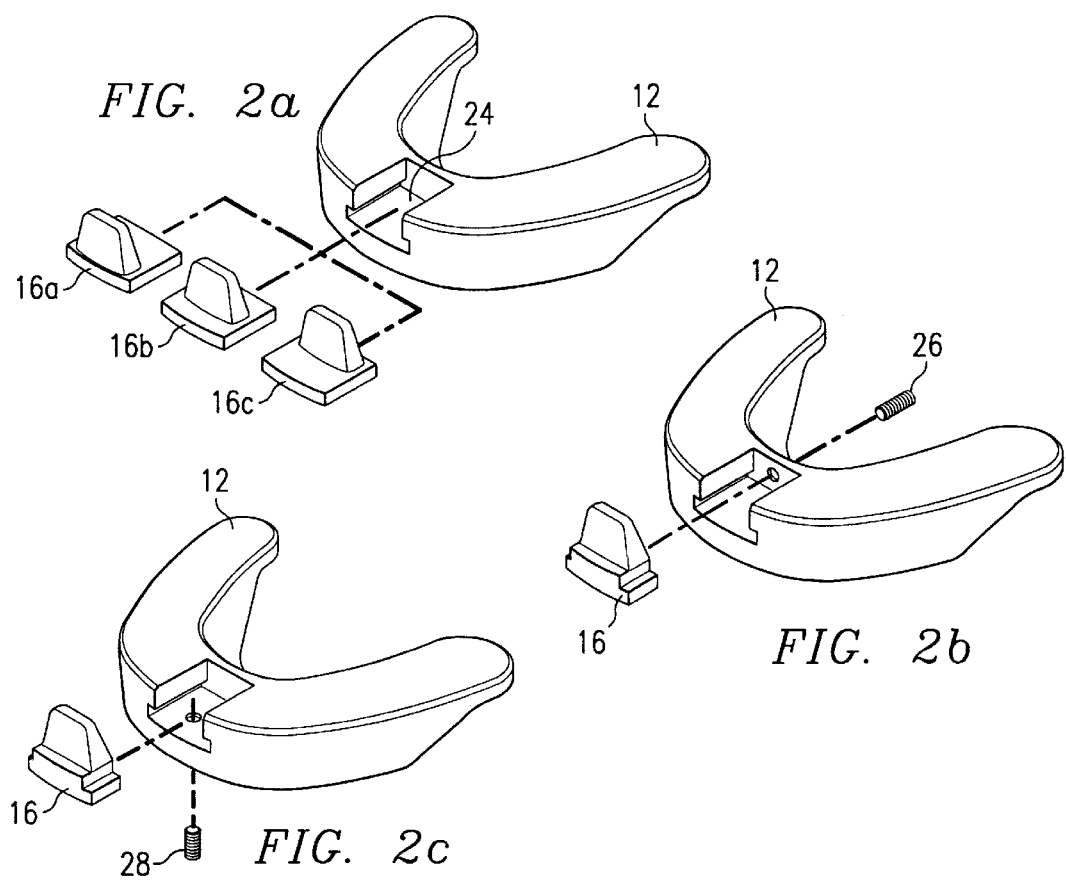

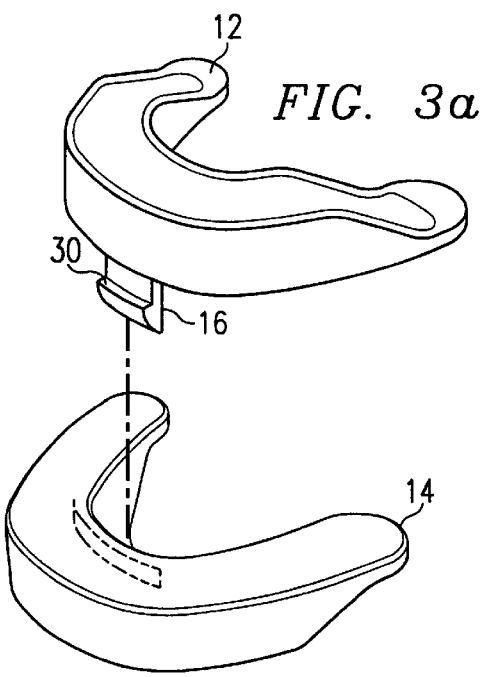
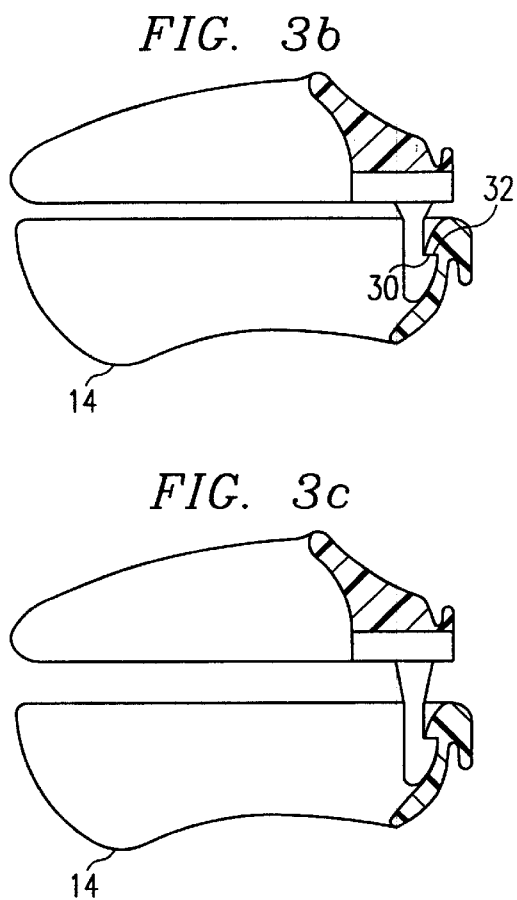
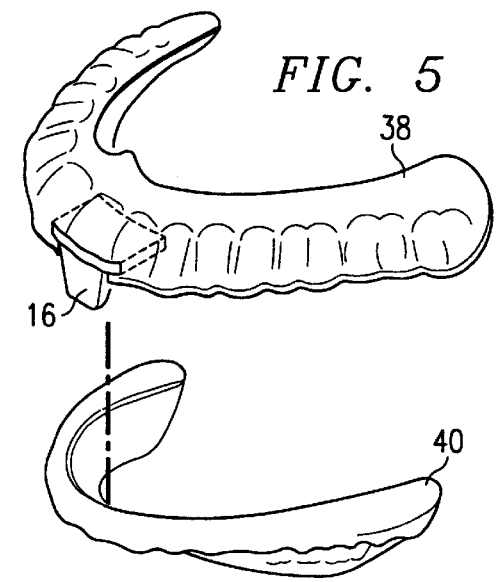
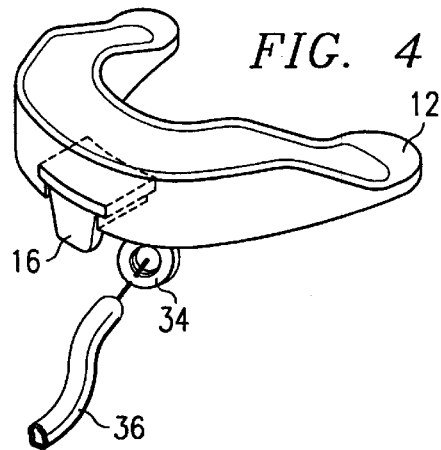

APPARATUS FOR PREVENTION OF SNORING AND IMPROVED BREATHING DURING SLEEP

CROSS REFERENCE TO RELATED APPLICATIONS

This application is a continuation of U.S. application Ser. No. No. 08/363,639, entitled "Apparatus for Prevention of Snoring and Improved Breathing During Sleep", and filed Dec. 22, 1994 by W. Keith Thornton, now abandoned, which is a continuation of U.S. application Ser. No. 08/129,598, entitled "Apparatus for Prevention of Snoring and Improved Breathing During Sleep" and filed Sep. 29, 1993 by W. Keith Thornton et al, now U.S. Pat. No. 5,427,117 issued Jun. 27, 1995.

TECHNICAL FIELD OF THE INVENTION

This invention relates generally to medical devices, and more particularly to an apparatus for the prevention of snoring and improved breathing during sleep.

BACKGROUND OF THE INVENTION

Snoring is a problem that plagues millions of people. And snoring affects not only the snorer, but also those within earshot of the snorer. Consequently, many attempts have been made to solve this snoring problem.

For example, U.S. Pat. No. 5,117,816 issued to Shapiro, et al., discloses an anti-snoring device that uses a single upper mouth piece with a flange extending downward to maintain the lower jaw in a forward position. Such devices are referred to as one-piece devices. The Shapiro, et al. patent takes advantage of the known technique of extending the lower jaw of a snorer, thereby opening the air passage and reducing or preventing snoring. Similar devices have also been disclosed in U.S. Pat. No. 5,003,994 issued Cook; U.S. Pat. No. 5,092,346, issued to Hayes, et al.

Because these patents disclose one piece devices, they present significant disadvantages. For example, to prevent snoring with these devices, the lower jaw must be held nearly stationary. This reduction in possible freedom of movement increases discomfort, an important consideration for any dental mouth piece.

One two-piece anti-snoring device has been discovered that uses the technique of extending the bottom jaw forward. That device also has certain disadvantages (a sample of that device is enclosed with an Information Disclosure Statement submitted herewith). In particular, it requires for customization by a dentist, thereby resulting in increased costs. Furthermore, the mechanism by which the lower jaw is extended forward is also not adjustable by the user, thereby resulting in possible discomfort as well as lack of effectiveness.

Therefore, a need has arisen for a dental device that will reduce or eliminate snoring and improve breathing during sleep, while at the same time provide a comfortable fit for the user.

Furthermore, a need has arisen for an anti-snoring device that can be custom-fit by the user, so as to eliminate costs that can result in customization of a dental fitting by a dental professional.

SUMMARY OF THE INVENTION

In accordance with the teachings of the present invention, a dental device is provided which substantially eliminates or reduces disadvantages and problems associated with prior art anti-snoring devices.

In particular, a dental device is provided which includes an upper arch with a deformable material in which a mold of the user's upper teeth is formed. Furthermore, a lower arch is included with a deformable material in which a mold of the user's lower teeth is formed. A post extends from the upper arch and contacts the lower arch so that the user's lower jaw is extended forward with respect to the user, thereby reducing snoring. In a particular embodiment, the forward location of the post, with respect to the user, is adjustable.

In another embodiment, the post is shaped to engage with the lower arch, so that the user's mouth cannot be opened more than a predetermined amount while the post is engaged. Furthermore, various embodiments can be combined, so that the forward location of the post is adjustable and the post is shaped to engage with the lower arch.

In still other embodiments of the present invention, an upper arch is provided that is fitted to the user's upper teeth. A moveable post extends from the upper arch and contacts either a lower arch or the user's teeth and gum to extend the user's lower jaw forward to reduce snoring. The moveable post is forwardly adjustable with respect to the user.

An important technical advantage of the present invention is the fact that a two-piece dental device is provided that is customizable. The two-piece embodiment provides significant comfort because of the freedom of movement it allows. Furthermore, its customizability, due to the deformable material used to form the teeth mold, makes the present invention inexpensive.

Another important technical advantage of the present invention is the forward adjustability in both the one-piece and two-piece embodiments. This forward adjustability allows for maximum comfort, as the forward location of the jaw can be set so as to prevent or reduce snoring, but not so far as to create discomfort.

Another important technical advantage of the present invention is the fact that the downwardly extending post may be shaped to engage with the lower arch, thereby preventing the mouth from opening while the post is engaged with the lower arch. This advantage helps prevent opening of the mouth and consequent retraction of the lower jaw.

BRIEF DESCRIPTION OF THE DRAWINGS

For a more complete understanding of the present invention and its advantages, reference is now made to the following description taken in conjunction with the accompanying drawings in which like reference numbers indicate like features and wherein:

FIG. 1 illustrates an isometric view of a two-piece anti-snoring device according to the teachings of the present invention;

FIGS. 2a–2d illustrate alternative embodiments of an adjustable post constructed according to the teachings of the present invention;

FIGS. 3a–3c illustrate alternative embodiments of an engaging post according to the teachings of the present invention;

FIG. 4 illustrates an embodiment of the of the present invention adapted for use in connection with a tube;

FIG. 5 illustrates another embodiment of a two-piece anti-snoring device constructed according to the teachings of the present invention;

DETAILED DESCRIPTION OF THE INVENTION

Figure 6A:
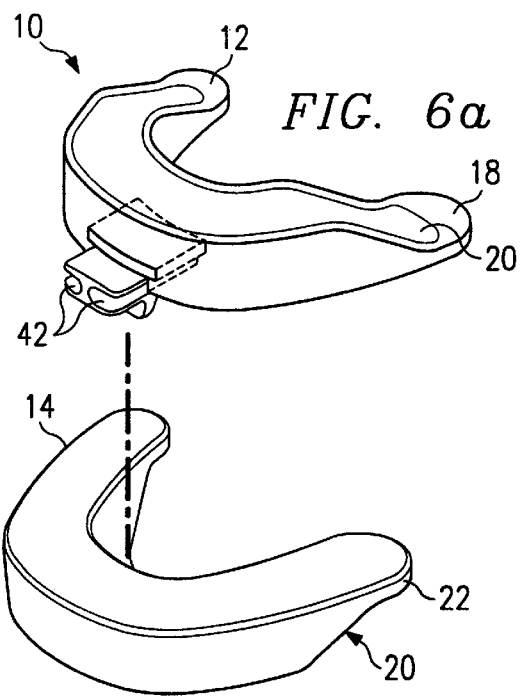
FIG. 6a and 6b illustrate embodiments of the present invention with breathing channels.

FIG. 1 illustrates a two-piece anti-snoring device 10 according to the teachings of the present invention. As shown in FIG. 1, the two-piece anti-snoring device 10 is provided with an upper arch 12 and a lower arch 14. "Two-piece" refers to the upper and lower arches 12 and 14. The upper arch 12 is inserted in a user's mouth, with the upper arch of teeth fitting in upper arch 12. Likewise, lower arch 14 is inserted in the user's mouth, with the lower arch of teeth fitting in lower arch 14. Upper arch 12 may fit over all or only some of the user's upper teeth. Likewise, lower arch 14 may fit over all or only some of the user's lower teeth.

Upper arch 12 is used in connection with downwardly extending post 16. Downwardly extending post 16 may be formed integrally with upper arch 12, or, as will be discussed below, may be an attachment to upper arch 12. Downwardly extending post 16, when in use, makes contact with lower arch 14. This contact causes lower arch 14, and consequently a user's lower jaw, to extend slightly forward. This forward extension allows the air passage of the user to remain open, thereby preventing snoring and improving breathing during sleep. Downwardly extending post 16 may have a wide range of shapes, including various lengths, depths, and widths, to perform this function. The term "post" is used to describe any such structure.

An important advantage of the anti-snoring device 10 is that is includes both an upper arch 12 and a lower arch 14. The use of these two arches allows for freedom of movement of the lower jaw. This movement is important because it provides comfort for the user. Prior art one piece devices do no allow for comfortable dental movement, such as side-to-side movement, since their posts engage with tissue in the user's mouth. Side-to-side movement with the present invention is provided because the downwardly extending post 16 may easily slide against lower arch 14.

In the embodiment shown in FIG. 1, upper arch 12 includes a tray 18 filled with a deformable material 20. Tray 18 may be made from any material suitable for dental uses, such as methylmethacrylate or a polycarbonate resin thermoplastic such as that sold under the Registered Trademark Lexan. Such materials are known to those familiar with dental mouthpieces, and other materials may be used without departing from the intended scope herein. Deformable material 20 is bonded to tray 18 and used for custom forming of a mold of the user's teeth for proper fitting during use. By using deformable material 20, each user can customize his or her anti-snoring device without the expense associated with having a dental mold prepared by a dental professional.

A suitable material for deformable material 20 is the ethylene-vinyl acetate copolymer resin sold under the Registered Trademark Elvax. Any other suitable deformable materials may also be used. Typically, with a material such as Elvax, the material 20 is heated to a temperature of about 150° Fahrenheit, through a microwave oven or by heating in hot water, for example, so as to place the material 20 in its deformable state. A user then inserts the arch 12 and bites down, thereby deforming the material 20 into the shape of the user's upper arch of teeth. The upper arch 12 is then removed and allowed to cool, thereby setting the material 20 into a mold of the user's upper arch.

Likewise, lower arch 14 includes a tray 22 filled with a deformable material 20. A mold of the lower arch of teeth is formed as described above in connection with upper arch 12.

FIGS. 2a–2c illustrate bottom views of various embodiments of upper arch 12 and downwardly extending post 16. These embodiments may be used with or without lower arch 14, and thus present both one-piece and two-piece embodiments, although only upper arch 12 is shown. As shown in FIG. 2a, the location of downwardly extending post 16 can be adjusted so as to adjust the distance that the lower jaw of a user extends forward. "Forward extension" refers to extension, with respect to a user, substantially from the user's back to front.

As shown in FIG. 2a, a particular embodiment for adjusting post 16 is to provide a plurality of posts, each with different post positions. Three such downwardly extending posts, 16a, 16b, and 16c, are shown. Downwardly extending post 16a will result in the lower jaw extending farther forward than that caused by downwardly extending post 16b. Similarly, downwardly extending post 16c will result in the lower jaw extending a shorter distance forward than that caused by either posts 16a or 16b. Posts 16a, 16b, and 16c are shown for purposes of example only, it being understood that posts causing less or more forward extension of the lower jaw may be used without departing from the intended scope of the present invention.

Downwardly extending posts 16a, 16b, or 16c are inserted into upper arch 12 by sliding them into slot 24. The particular slot 24 shown in FIG. 2a is exemplary only, and other sized slots can be used without departing from the intended scope of the present invention. Likewise, the post 16 may be affixed to upper arch 12 by other techniques and structures without departing from the intended scope of this invention. Similarly, upper arch 12 may be formed integrally with downwardly extending post 16 in a predetermined location.

By adjusting the relative location of downwardly extending post 16, the degree to which the user's lower jaw is extended forward is adjusted. This adjustment allows for greater comfort for the user, and also allows for a user to determine how far forward the lower jaw must be extended so as to prevent or diminish snoring, while maintaining comfort.

FIGS. 2b and 2c illustrate alternative embodiments for adjusting the relative position of downwardly extending post 16. As shown in FIG. 2b, the position of downwardly extending post 16 may be adjusted by set screw 26. Set screw 26 acts as a backstop for downwardly extending post 16. As set screw 26 is set farther, downwardly extending post 16 will be pushed farther forward, thereby resulting in greater forward extension of the lower jaw. FIG. 2c illustrates an alternative embodiment in which set screw 28 contacts downwardly extending post 16 from the top, thereby fixing downwardly extending post 16 in place. Set screw 28 could also contact downwardly extending post 16 at the bottom or side to accomplish the same function.

FIGS. 2a, 2b, and 2c illustrate various embodiments of the present invention in which the position of downwardly extending post 16 may be adjusted either forward or backward. It should be understood that the particular techniques disclosed for providing this adjustment are exemplary only, and other techniques and structures may be used without departing from the intended scope of the present invention.

As discussed, FIGS. 2a, 2b, and 2c illustrate embodiments both for one-piece and two-piece devices. For the two-piece embodiments, post 16 contacts the lower arch 14. for the one-piece embodiments, post 16 contacts the lower teeth and gums.

FIG. 2d illustrates another two-piece embodiment for adjusting the forward position of the lower jaw. As shown in FIG. 2d, during use, post 16 contacts stop 29 of lower arch 14. Stop 29 is adjustable, thereby allowing adjustment of the forward position of lower arch 14. Stop 29 can be adjusted, for example, through use of a set screw 31. Stop 29 may be adjusted in other ways, as well, without departing from the intended scope of the present invention. For example, a plurality of stops 29, each with different stop positions can be provided, similarly to the posts of FIG. 2a. Any one of such steps can be inserted to adjust the forward position of lower arch 14, and thus the lower jaw, for comfort and successful operation.

FIG. 3a illustrates another two-piece embodiment of the present invention in which downwardly extending post 16 is shaped so as to allow engagement with lower arch 14. This engagement is for the purpose of preventing a user's mouth from opening too wide during use. If a user's mouth opens too wide during use, the downwardly extending post may no longer be in contact with lower arch 14, resulting in retraction of the bottom jaw. A particular embodiment for achieving this is shown in FIGS. 3a and 3b. As shown, the downwardly extending post 16 latches with a recess in lower arch 14. In particular, downwardly extending arch 16 is formed with a shoulder 30 that engages with matching shoulder 32 of lower arch 14. As shown in FIG. 3a, the recess of lower arch 14 is elongated so as to allow side-to-side movement of downwardly extending post 16, allowing for comfortable side-to-side movement of both upper arch 12 and lower arch 14. It should be understood that shoulders 30 and 32 may be also formed as part of a grooved or elliptical engagement structure, or any other structure that accomplishes the engagement function, without departing from the intended scope of this invention.

FIG. 3c illustrates an embodiment in which the length of downwardly extending post 16 may be adjusted. With a longer downwardly extending post 16, the engagement of downwardly extending post 16 with lower arch 14 will occur with the mouth wider open. This adjustment capability in the length of downwardly extending post 16 allows for customization of the fit and increased comfort.

The particular structure discussed in connection with FIGS. 3a–3c is illustrative only. It should be understood that other structures may be used to allow downwardly extending post 16 to engage with lower arch 14. The function of the engagement, as discussed above, is to reduce the likelihood that a user will open his or her mouth during sleep, causing retraction of the lower jaw and possible snoring.

The embodiments discussed in connection with FIGS. 2a–2c, in which the relative forward position of the downwardly extending post 16 is adjustable, may also be used in connection with the embodiments discussed in FIGS. 3a–3c. Thus, the ability of downwardly extending post 16 to engage with lower arch 14 may be combined with adjusting the relative forward position of downwardly extending post 16.

FIG. 4 illustrates an alternative embodiment of the present invention in which a tube loop 34 is provided for use in connection with upper arch 12 and downwardly extending post 16. Tube loop 34 secures a tube 36. Tube 36 may allow for the flow of a gas, such as oxygen. Tubes such as tube 36 are used with sleep apnea patients to ensure the proper supply of oxygen to the user. Tube loop 34 may be formed integrally with upper arch 12, integrally with downwardly extending post 16, or may be formed as an attachment to either upper arch 12 or downwardly extending post 16. Likewise, tube loop 34 could be formed in connection with or attached to lower arch 14 for the two-piece embodiments.

FIG. 5 illustrates an alternative to the embodiment of the present invention in which a mold of the user's teeth is made by a dental professional. Thus, the deformable material 20 is not used. The embodiment shown in FIG. 5 may be made of a suitable dental material, such as methylmethacrylate. The downwardly extending post 16 may be formed integrally with upper arch 38 or may be formed as an insert as discussed above in connection with FIGS. 2a–2c. Furthermore, downwardly extending post 16 of the embodiment shown in FIG. 5 may be formed so as to perform all the functions discussed above in connection with FIGS. 2a–2c, and FIGS. 3a–3c. Likewise, a loop 34 for securing a tube for supply of a gas may also be formed integrally or attached to either upper arch 38, lower arch 40, or downwardly extending post 16 of FIG. 5. Upper arch 38 and post 16 may be used either with or without lower arch 40.

FIG. 6a illustrates an alternative embodiment of the present invention that includes breathing channels 42. Breathing channels 42 may be formed integrally with downwardly extending post 16, upper arch 12, or lower arch 14. The purpose of these breathing channels is to provide a clear passage way for breathing during use. These breathing channels 42 may be combined with any of the previously discussed embodiments of the present invention. Breathing channels 42 extend forward to separate the user's lips so as to allow air passage through the mouth. Such breathing channels will assist in the prevention of snoring and assist in the treatment of sleep apnea. It should be understood that the particular structure of the breathing channels shown in FIGS. 6a and 6b is exemplary, and other structures may be used without departing from the intended scope of the present invention.

Figure 6B:
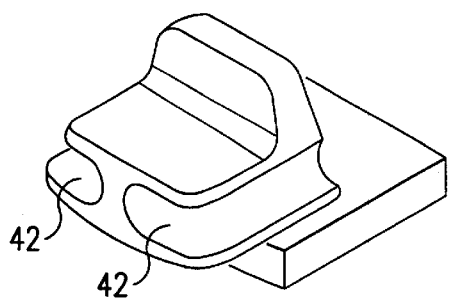

FIG. 6b illustrates an embodiment of post 16 formed with breathing channels 42. As shown in FIG. 6b, the breathing channels 42 are disposed on either or both sides of downwardly extending post 16 to provide a clear passage way for breathing.

Figure 7:
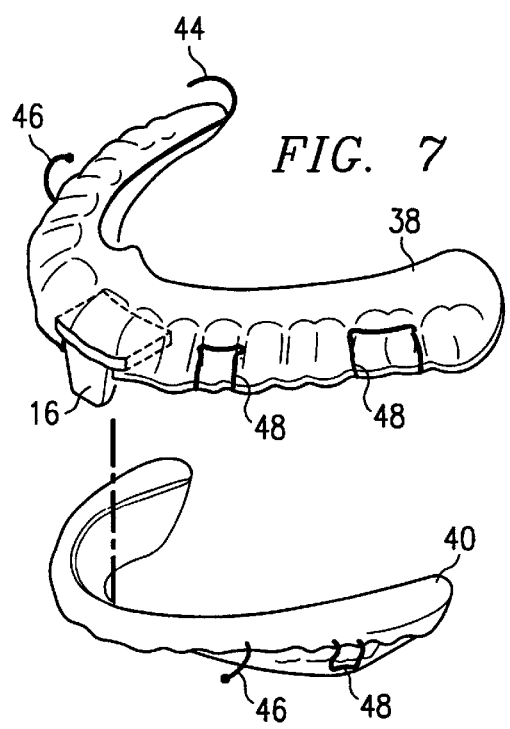
FIG. 7 illustrates an embodiment of the present invention with securing clasps.

FIG. 7 illustrates another embodiment of the present invention in which the upper arch 38 and lower arch 40 may be more fully secured to the user's teeth for use of various clasps. As shown in FIG. 7, various clasps can be used to secure the upper and lower arches. Illustrative embodiments include C clasps 44, ball clasps 46, and U clasps 48. Such clasps may be used with any of the embodiments disclosed above.

Although the present invention and its advantages has been described in detail, it should be understood that various changes, substitutions and alterations can be made herein without departing from the spirit and scope of the invention as defined by the appended claims.

What is claimed is:

1. An oral appliance, comprising:
    an upper arch including a deformable material in which a mold of one or more of a user's upper teeth may be formed, the upper arch further including a downwardly extending post; and
    a lower arch including a deformable material in which a mold of one or more of the user's lower teeth may be formed, the lower arch uncoupled from the upper arch until the appliance is inserted into the user's mouth, the post contacting a surface of the lower arch after the appliance is inserted into the user's mouth to cause the user's lower jaw to extend forward from its natural position.

2. The appliance of claim 1, wherein the forward location of the lower arch is adjustable while the appliance is inserted into the user's mouth.

3. The appliance of claim 1, wherein the post is forwardly adjustable.

4. The appliance of claim 1 further comprising an adjustable stop coupled to the lower arch, the post operable to contact the adjustable stop.

5. The appliance of claim 1, wherein:

the upper arch includes a slot; and the post is operable to engage the upper arch using the slot.

6. The appliance of claim 5, further comprising a plurality of posts, only one of which is engaged with the upper arch at any one time, the posts having different forward locations with respect to the user when engaged with the upper arch.

7. The appliance of claim 1, further comprising a set screw operable to adjust the forward position of the post.

8. The appliance of claim 1, wherein the appliance is operable to cause the user's lower jaw to extend forward to a fixed forward position.

9. The appliance of claim 1, wherein the post is operable to engage the lower arch.

10. The appliance of claim 9, wherein:

the post includes a first shoulder; and the lower arch includes a second shoulder operable to engage the first shoulder.

11. The appliance of claim 1, wherein the appliance accommodates lateral movement of the lower jaw.

12. An oral appliance, comprising:

an upper arch adapted to receive one or more of a user's upper teeth and including a downwardly extending post, the upper arch leaving the most posterior upper teeth exposed; and a lower arch uncoupled from the upper arch until the appliance is inserted into the user's mouth, the lower arch adapted to receive one or more of the user's lower teeth, the lower arch leaving the most posterior lower teeth exposed, the post operable to contact a surface of the lower arch after the appliance is inserted into the user's mouth to cause the user's lower jaw to extend forward from its natural position, the appliance operable to maintain a separation between the most posterior lower teeth and the most posterior upper teeth.

13. The appliance of claim 12, wherein the forward location of the lower arch is adjustable while the appliance is inserted into the user's mouth.

14. A method of treating a user's breathing disorder using an oral appliance, comprising:

inserting an upper arch into the user's mouth, the upper arch comprising a mold of one or more of the user's upper teeth formed using a deformable material, the upper arch further comprising a downwardly extending post;

inserting a lower arch into the user's mouth, the lower arch comprising a mold of one or more of the user's lower teeth formed using a deformable material, the lower arch uncoupled from the upper arch;

contacting, with the post, a surface of the lower arch after the upper arch and the lower arch have been inserted into the user's mouth; and causing the user's lower jaw to extend forward from its natural position for purposes of treating the user's breathing disorder.

15. The method of claim 14, further comprising adjusting the forward position of the lower arch while the oral appliance is inserted into the user's mouth.

16. The method of claim 14, wherein the user's lower jaw is extended forward to a to a fixed forward position.

17. The method of claim 14, wherein contacting the surface of the lower arch comprises contacting, with the post, an adjustable stop coupled to the lower arch.

18. The method of claim 14, further comprising adjusting the forward position of the post while the oral appliance is inserted into the user's mouth.

19. The method of claim 14, further comprising engaging the lower arch with the post.

20. The method of claim 14, further comprising accommodating lateral movement of the lower jaw while the oral appliance is inserted into the user's mouth.

* * * * *